United States Patent [19]

Kistner et al.

[11] Patent Number: 5,698,433
[45] Date of Patent: Dec. 16, 1997

[54] METHOD FOR PRODUCING INFLUENZA VIRUS AND VACCINE

[75] Inventors: Otfried Kistner, Vienna; Noel Barrett, Kolsterneuburg/Weidling; Wolfgang Mundt; Friedrich Dorner, both of Vienna, all of Austria

[73] Assignee: Immuno AG, Vienna, Austria

[21] Appl. No.: 684,729

[22] Filed: Jul. 22, 1996

Related U.S. Application Data

[63] Continuation of Ser. No. 338,761, Nov. 10, 1994, abandoned.

[51] Int. Cl.[6] ............................. C12N 7/02; A61K 39/00
[52] U.S. Cl. ................... 435/239; 435/235.1; 424/209.1
[58] Field of Search ................. 424/209.1; 435/235.1, 435/239

[56] References Cited

U.S. PATENT DOCUMENTS

| | | | |
|---|---|---|---|
| 4,072,565 | 2/1978 | Weiss et al. | 435/325 |
| 4,205,131 | 5/1980 | Almedia | 435/325 |
| 4,500,513 | 2/1985 | Brown et al. | 424/209.1 |
| 4,525,349 | 6/1985 | Montagnon et al. | 424/89 |
| 4,664,912 | 5/1987 | Wiktor et al. | 424/89 |
| 4,783,411 | 11/1988 | Gabliks | 435/237 |
| 4,927,762 | 5/1990 | Darfler | 435/325 |
| 5,147,790 | 9/1992 | Wilson | 435/70.3 |
| 5,316,938 | 5/1994 | Keen et al. | 435/325 |
| 5,391,491 | 2/1995 | Mundt et al. | 435/325 |
| 5,393,668 | 2/1995 | Cinatl et al. | 435/325 |

FOREIGN PATENT DOCUMENTS

| | | |
|---|---|---|
| 0115442A2 | 8/1984 | European Pat. Off. . |
| 0019218 | 11/1980 | WIPO . |
| 0113665 | 7/1984 | WIPO . |
| WO 91/03552 | 3/1991 | WIPO . |
| WO91-09937 | 7/1991 | WIPO . |
| 0485689 | 5/1992 | WIPO . |

OTHER PUBLICATIONS

Cinatl et al. Arch Virol 125: 327–330 (1992).
Cinatl et al. Intervirology 37:361–366 (1994).
Cinatl et al. Biology International, vol. 17: No. 9 (1993).
Nakamura et al. J. Gen. Virol. 56: 199–202 (1981).
Lau et al. Virology 212:225–231 (1995).
Vey et al. J. Virol. 188:1 408–411 (1992).
Merten et al. Cytotechnology 14: 47–59 (1994).
Merten et al. Biologicals 23: 185–189 (1995).
Swanson et al. Journal of Biological Standardization 16:311–320 (1988).
Levenbrook et al. Journal of Biological Standardization 12; 391–398 (1984).
Contreras et al. In Vitro Cellular & Developmental Biology 21(11):649–652 (1985).
Johnson et al. Develop. biol. Standard. 50: 27–35 (1982).
Katz et al. The Journal of Infectious Diseases 160(2): 191–198 (1989).
Kaverin et al. The Journal of Virology, 69(4): 2700–2703 (1995).
Govorkova et al. The Journal of Infectious Diseases 172: 250–253 (1995).
Bulletin of the World Health Organization 73(4): 431–435 (1995).
Vincent-Falquet et al. Develop. biol. Standard. 70: 153–156 (1989).
Enami et al. Proc. Natl. Acad. Sci. USA 87: 3802–3805 (1990).
Luytjes et al. Cell 59: 1107–1113 (1989).
Robertson et al. Journal of General Virology 72:2671–2677 (1991).
Scild et al. Nature 303: 706–709 (1983).
Tomas et al., Rev. Roum. Med. Virol., 1981, vol. 32(2): pp. 145–154.
Klenk et al. "The Molecular Biology of Influenza Virus Pathogenicity", pp. 247–281, Academic Press (1988).
Edsall et al. "Requirements For Inactivated Influenza Vaccine", WHO: Technical Report Series, 384:41–56 (1968).
Steineke-Gröber et al. "Influenza virus hemagglutinin with multibasic cleavage site is activated by furin . . . ", The EMBO Journal, 11:2407–2414 (1992).
Lazarowitz et al. "Enhancement of the Infectivity of Influenza A and B Viruses by Proteolytic Cleavage . . . ", Virology, 68:440–454 (1975).
Hirst "The Agglutination Of Red Cells By Allantoic Fluid Of Chick Embryos Infected With Influenza Virus", Science, 94:22–23 (1941).
Barrett et al. "Viruses", Methods of Immunological Analysis, 2:115–132 (1993).

(List continued on next page.)

Primary Examiner—George C. Elliott
Assistant Examiner—Matthew Latimer
Attorney, Agent, or Firm—Foley & Lardner

[57] ABSTRACT

A method of producing an influenza virus and vaccines derived from the virus utilizes cultured vertebrate biomass aggregates comprising a plurality of cell types derived from a plurality of vertebrate tissues and is particularly suitable for use with chicken embryo cultures. The method both eliminates the necessity to use costly methods requiring whole chicken embryos and provides proteases suitable for the activation of a wide variety of viruses. After infecting the cells of the culture with an influenza virus, which is preferably modified to create a cleavage site in the hemagglutinin of the virus, a substance such as a protease is introduced that cleaves the hemagglutinin. The culture then is incubated under conditions that permit growth of the virus. The method provides also for the augmentation of virus activation in the culture by the continuous or batchwise removal of culture media, treatment of the media with substances such as proteases which increase cellular activation, attenuation of any undesired effects of the augmentation and return of the augmented media to the culture. The vaccines produced from the harvested virus therefore are free of egg proteins and are much more economical to produce. The methodology of the present invention allows the large scale continuous production of many viruses to a high titre.

13 Claims, No Drawings

OTHER PUBLICATIONS

Scholtissek et al. "Multiplication of Influenza A Viruses with Cleavable and Non–cleavable Haemagglutinin...", *J. Gen. Virol.*, 69:2155–2165 (1988).

Barr "Mammalian Subtilisins: The Long–Sought Dibasic Processing Endoproteases", *Cell*, 66:1–3 (1991).

Burnet "Influenza Virus Infections Of The Chick Embryo By The Amniotic Route", *Austr. Jnl. Experimental Biology and Medical Science*, 18:353–360 (1940).

Ohuchi et al., Journal of Virology, 65(7): 3530–3537 (Jul. 1991).

Boehringer Mannheim Catalog, pp. 191–195 (1994).

METHOD FOR PRODUCING INFLUENZA VIRUS AND VACCINE

This application is a continuation of application Ser. No. 08/338,761, filed Nov. 10, 1994, now abandoned.

FIELD OF THE INVENTION

The present invention relates to the production of influenza viruses in culture and vaccines derived therefrom.

BACKGROUND OF THE INVENTION

Influenza is a major respiratory disease in man and is responsible for many thousands of deaths every year.

There are three general types of influenza viruses, Type A, Type B and Type C. The types are defined by the absence of serological crossreactivity between their internal proteins. Influenza Type A viruses are further classified into sub-types based on antigenic differences of their glycoproteins, the hemagglutinin (HA) and neuraminidase (NA) proteins. Man is susceptible to diseases caused by infection with Influenza Types A, B, and C viruses.

Currently, the most significant causes of influenza infections in humans are those attributable to Type B and to subtypes H1N1 and H3N2 of influenza type A. Because of this, antigens of Type B and of subtypes H1N1 and H3N2 of Influenza Type A are those which are generally incorporated into present influenza vaccines. The vaccines currently available have protection rates ranging from 75–90%.

The influenza HA antigen is the major target for the protective immune responses of the host to the virus. One of the problems in the development of effective influenza vaccines stems from the high mutation rate of the gene coding for the HA protein, resulting in frequent charges in its antigenicity. Therefore, in order to produce effective vaccines, new vaccines from recent influenza isolates must be produced frequently.

The normal practice of recovering new viral isolates involves recovery with a throat swab or similar source, followed by cultivation of the isolates in embryonated chicken eggs. Although the initial isolation into eggs may be difficult, the virus adapts to its egg host, and large scale production of the virus can be carried out in eggs.

Conventional methods for producing influenza vaccine have typically involved the growth of the viruses in embryonated chicken eggs. Viruses grown by this method are then used for producing live attenuated virus, killed whole virus or subunit vaccines. Conventional methodology involving embryonated chicken eggs to produce influenza vaccine, however, is extremely cumbersome, involving the handling of many thousands of eggs per week. In a typical operation, eggs must be candled, the shells must be sterilized and each egg must be inoculated by injection of a small volume of virus into the allantoic cavity. The injected eggs then are incubated for 48–72 hours at 33°–37° C., candled again, refrigerated overnight and opened to allow harvesting of the allantoic fluid. The harvested fluid must then be clarified by filtration and/or centrifugation before processing for further purification. Extensive purification is then required to ensure freedom from egg protein. *Requirements For Inactivated Influenza Vaccine,* World Health Organization Technical Report Series, 384 (1966).

In a typical chicken embryo operation, between one and two eggs are required to produce one dose of influenza vaccine. Thus, to produce a million doses of vaccine, more than a million egg embryos must be processed. In sum, conventional technology for producing influenza virus vaccines involves many steps which are difficult to automate and are, accordingly, labor intensive, time consuming and subject to contamination. Thus, a need exists for methods which are less labor intensive, require less biological tissue per dose produced and are less susceptible to contamination.

Many attempts have been undertaken previously in the art to utilize standard tissue culture technology with primary chicken embryo cell ("CEC") lines or established mammalian cell lines for influenza virus vaccine production. These attempts have proved unsuccessful because of the failure of a large number of viral strains to replicate in conventional CEC cultures. The use of established mammalian cell lines such as MDCK has been more successful in replicating some strains. However, a number of virus strains will not replicate in the MDCK line. Another disadvantage of MDCK relates to its transformed nature. Fears about possible adverse effects of the use of transformed cells for human vaccine production make MDCK a disfavored cell line for human vaccine production.

One of the primary difficulties in growing a number of influenza strains in primary tissue culture or established cell lines arises from the necessity for proteolytic cleavage activation of the influenza hemagglutinin in the host cell. Cleavage of the virus $HA_0$ precursor into the HA 1 and HA 2 subfragments is required in order to convert new virus particles produced in the host cell into virions capable of infecting new cells because this cleavage plays a key role in the entry of the virion into the new cell. Cleavage is known to occur during transport of the integral $HA_0$ membrane protein from the endoplasmic reticulum of the infected cell to the plasma membrane. In the course of transport, hemagglutinin undergoes a series of co-and post-translational modifications including proteolytic cleavage of the precursor HA into the aminoterminal fragment HA 1 and the carboxyterminal HA 2.

The fact that influenza virions have been found which contain either uncleaved or cleaved HA glycoproteins indicates that cleavage is not always necessary for virus assembly and release from the infected cell. Cleavage of HA is necessary, however, for the initiation of infection of a new host cell.

Although it is known that an uncleaved HA can mediate attachment of the virus to its neuramic acid containing receptors at the cell surface it is not capable of the next step in the infectious cycle i.e., fusion. It has been reported that exposure of the hydrophobic amino terminus of the HA 2 by cleavage is required so that it can be inserted into the target cell, thereby forming a bridge between virus and target cell membrane. This is followed by fusion of the two membranes and entry of the virus into the target cell.

Proteolytic activation of hemagglutinin follows a pattern observed with many enzymes and hormone precursors, such as proinsulin, progastrin and proopiomelanocortin. It involves cleavage at an arginine residue by a trypsin like endoprotease. The available evidence suggests that the endoprotease is an intracellular enzyme which is calcium dependent and has a neutral pH optimum. However beyond that, little is known about the nature of the intracellular protease (Klenk and Rott, 1988).

Since the activating proteases are cellular enzymes, the infected cell type determines whether or not hemagglutinin is cleaved. The hemagglutinins of the mammalian influenza viruses and the nonpathogenic avian influenza viruses are susceptible to proteolytic cleavage only in a restricted number of cell types. On the other hand, the hemagglutinins of pathogenic avian viruses among the H 5 and H 7 subtypes are cleaved by proteases present in a broad range of different host cells. Thus, there are differences in host range resulting from differences in hemagglutinin cleavability which can be correlated with the pathogenic properties of the virus.

The differences in cleavability are due to differences in the structure of the cleavage site of the hemagglutinin. Sequence analyses have revealed that the HA1 and HA2 fragments of the hemagglutinin molecule of the pathogenic avian and of all mammalian influenza viruses are linked by a single arginine. This is in contrast to the pathogenic avian strains, which have a sequence of several basic amino acids at the cleavage site with the common denominator lysine-arginine or arginine-arginine. Although the hemagglutinins of all influenza viruses are cleaved by the same general mechanism, resulting in the elimination of the basic amino acids, it has to be assumed that differences exist in the specificities of the proteases, which recognize either a single arginine or the paired basic residues lysine-arginine and arginine-arginine.

The protease activities that are essential for cleavage of a broad range of influenza virus strains are available in vertebrate cells such as the whole embryonated egg. In contrast, conventional CEC cultures prepared from chick embryos will allow replication of only a narrow range of influenza virus strains.

The standard procedures for preparation of CEC cultures include removal of the head and inner organs and multiple trypsinization steps resulting in a highly selected cell population consisting mainly of fibroblasts. Standard fibroblast cultures are not satisfactory for the replication of many different virus strains, however. Therefore, a need exists for means and methods for increasing the efficiency of virus production.

Some attempts at improving influenza virus production have focused on the use of exogenous enzymes. For example, it has been reported that the limited replication of several influenza A strains in standard CEC cultures could be overcome by the addition of trypsin to the tissue culture medium. Trypsin addition significantly increases the infectivity of various strains grown in CEC cultures (Lazarowitz and Choppin, 1975). In addition, Stieneke-Gröber et al. (1992) have identified the HA activating enzyme in MDCK cells as a furin-like protease. Such enzymes have been isolated from human and mouse tissues and constitute a new family of eukaryotic subtilisin-like endoproteases. These findings indicate that the proteases responsible for the activation of viral glycoproteins at multibasic cleavage sites are subtilisin-like enzymes.

Gabliks, U.S. Pat. No. 4,783,411, discusses a method for preparing influenza-A vaccines in goldfish cell cultures. Of necessity, the virus particles for infecting the Gabliks' cultures after their establishment were obtained from chicken embryo cultures or from infected CD-1 strain mice. The virus is passaged at least twice in such cultures, resulting in an attenuated virus which may be used as a live vaccine.

U.S. Pat. No. 4,500,513 to Brown et al. discloses the production of virus particles for making vaccine from liquid cell culture or cell monolayer culture wherein a protein hydrolyzing enzyme such as trypsin, chymotrypsin or carboxypeptidase is incubated with a partially infected culture to increase the proportion of additional cells infected by the virus and to assure the maximum cytopathic effect. Harvesting of the virus is performed at a point in the growth phase of the virus which exhibits maximum cytopathic effect. All of the examples of Brown describe a dog kidney cell line which is not usable for human vaccine production, however.

SUMMARY OF THE INVENTION

It is an object of the present invention to provide for the efficient production of viruses from cultured cells and to provide for the production of vaccines from those viruses.

It is a further object of the present invention to provide a method for the continuous production of virus particles from a sustained culture of vertebrate biomass aggregates and, optionally, to modify a subject influenza virus to create a cleavage site in the hemagglutinin of the influenza virus.

It is also an object of the present invention to provide a method and means for optimizing the activity of a virus in culture by augmentation with exogenous enzymes.

In order to achieve these and other objects, there is provided, in accordance with one aspect of the present invention, a method of producing an influenza virus wherein the method comprises the steps of (A) providing a culture that is comprised of vertebrate cells and culture media, wherein the cells comprise a plurality of cell types and wherein the cell types possess substantially all the viral infection factors necessary for activation of the virus for infection of other cells; (B) infecting the vertebrate embryo cells of the culture with an influenza virus; and then (C) incubating the culture under conditions permitting growth of the influenza virus.

In accordance with another aspect of the invention, a method is provided that is particularly useful when the vertebrate cells are aggregates and, most advantageously, when the cells are a plurality of types from vertebrate embryos. Most preferably, the method of the invention comprises using a plurality of types of cells from chicken embryos.

In accordance with additional aspects of the invention, the vertebrate cells are provided in cultures of cell aggregates wherein the aggregates have a diameter between about 100 µm and 1000 µm, preferably between about 300 µm to about 800 µm and more preferably between about 400 µm to about 700 µm. Preferable cultures of the invention comprise chicken embryo cell aggregates, influenza virus and a substance that cleaves influenza hemagglutinin.

In accordance with still another aspect of the invention, a method is provided that is particularly advantageous wherein the cells are derived from a vertebrate embryo in a particular phase of ontogenetic development wherein the cells are at peak metabolic activity.

In accordance with yet another aspect of the invention, a method is provided that further comprises, after step (B) and before step (C), if necessary, the step of (D) introducing into the culture media a substance that augments the activation of the virus. Preferably, the introduced substance cleaves influenza hemagglutinin.

In accordance with other aspects of the method of the invention, the substance provided that cleaves influenza hemagglutinin is a protease, preferably from the trypsin family or the family of subtilisin-like proteases, preferably trypsin, chymotrypsin, thermolysin, pronase or subtilisin A.

In accordance with further aspects of the method of the invention, a substance is provided which inactivates the protease after its incubation with the media, cells or both, in order to eliminate or attenuate the negative or toxic effects of the protease on the cultured cells.

In accordance with yet additional aspects of the invention, the method further comprises the steps of (E), harvesting the influenza virus from the culture, (F), preparing a vaccine with the harvested influenza virus, and (L) treating vertebrates prophylactically with the vaccine in order to prevent infection of the vertebrate with the virus.

In accordance with yet another aspect of the invention, a method is provided which comprises, when necessary, for the periodic or continuous removal of the virus containing culture media into an augmentation loop for the introduction into the culture media of a substance, such as protease selected from the trypsin family or the family of subtilisin-like proteases, preferably, trypsin, chymotrypsin, thermolysin, pronase or subtilisin A, that augments the activation of the virus. The method provides further for the inactivation or inhibition of the trypsin or Subtilisin A so that any toxic effects of the trypsin or Subtilisin A are eliminated while increased activation of the virus is achieved.

In accordance with still another aspect of the present invention, an Influenza virus or viruses produced by the method of the invention as well as vaccines to the produced influenza virus are provided.

BRIEF DESCRIPTION OF THE TABLES

In the tables, B/Massachusetts refers to B/Massachusetts/71; B/Panama refers to B/Panama/45/90; B/Yamagata refers to B/Yamagata/16/88; Brazil refers to A/Brazil/11/78 (H1N1); California refers to A/California/10/78 (H1N1); Singapore 6 refers to A/Singapore/6/86 (H1N1); Taiwan refers to A/Taiwan/1/86 (H1N1); Texas 36 refers to A/Texas/36/91 (H1N1); USSR refers to A/USSR/90/77 (H1N1); A2 Singapore refers to A/Singapore/1/57 (H2N2); Beijing refers to A/Beijing/353/89 (H3N2); Guizho refers to A/Guizho/54/89 (H3N2); Hong Kong refers to A/Hong Kong/1/68 (H3N2); Hong Kong 5 refers to A/Hong Kong/5/83 (H3N2); Shanghai 16 refers to A/Shanghai/16/89 (H3N2); Texas refers to A/Texas/1/77 (H3N2); and Victoria refers to A/Victoria/3/75 (H3N2).

Table 1 compares the hemagglutinin A titre obtained from various influenza strains produced by embryonated eggs and those produced in spinner culture with and without the proteases trypsin and subtilisin A.

Table 2 compares the virus yields per egg produced by conventional embryonated egg technology and by those produced according to the present invention in biomass culture with and without the proteases trypsin and subtilisin A.

Table 3 presents data which demonstrates the scale-up of a system according to the invention from 100 ml cultures to an automated 2 liter fermentor.

Table 4 compares the yield of HA antigen obtained for different strains of influenza A and a B strain in MDCK cell culture, standard CEC culture and CEC biomass aggregates in the presence and absence of trypsin and subtilisin.

Table 5 compares the antibody titres to four strains of influenza virus obtained in mice following immunization with conventional embryonated-egg-derived vaccines with titres produced by vaccines produced in a biomass fermentor according to the present invention.

DETAILED DESCRIPTION OF THE PREFERRED EMBODIMENTS

To increase the degree of infectivity in standard CEC primary cultures, the present inventors have developed a novel methodology for preparing vertebrate cell biomass for the production of viruses. In one aspect, the methodology of the present invention involves the preparation of cell aggregates representing a plurality of cell types suspended in culture medium, which aggregates are in a range of diameters suitable for maximizing the metabolic activity of the cells to thereby produce large quantities of virus. Moreover, by providing a plurality of cell types, the method of the invention ensures that the proteases necessary for the activation of virtually any influenza strain are present.

The present invention represents an improvement over the prior art in that it employs vertebrate cell aggregates comprising a plurality of cell types. A "plurality of cell types" according to the present invention might include cells derived from organs such as the brain, liver and pancreas, from tissues such as those of the oropharyngeal cavity, and from nerve and connective tissues. A culture of cells according to the invention thus contains collectively the metabolic machinery of many or all of the tissues and organs of a vertebrate embryo. The consequent supply of a plurality of different types and classes of cellular proteases allows activation of a broad range of viruses.

Hence, the primary cultures of the present invention provide a collection of differentiated cell types, that is, a plurality of cell types which contain collectively the metabolic machinery of an entire vertebrate embryo or those portions of the embryo necessary to culture efficiently a desired virus. Because a plurality of cell types includes many different proteases, the cultures of the present invention enable activation of a broad range of influenza viruses. The presence of a plethora of cell types mimics an entire vertebrate embryo or the necessary portions thereof but lacks the disadvantages of the whole embryo. Thus, the availability of a multiplicity of proteases in the present invention allows replication of virtually all vaccine strains.

If a particular strain cannot be activated in this system by endogenous enzymes alone, activation can be achieved by addition of extraneous proteases such as trypsin or subtilisin A. In addition, the invention provides for the use of proteases such as trypsin at much higher concentrations than those normally tolerated by cells in culture, thereby further increasing the level of HA activation.

This increase in the level of infection activation is achieved by use of an "augmentation loop," whereby portions of virus-containing media, cells or both from a cell fermentor containing cells cultured and infected according to the present invention are periodically or continually removed to a vessel or column containing one or more proteases such as trypsin. After a certain incubation time, the removed media, cells or both are transferred to a vessel containing a substance which inhibits the protease activity, and media is subsequently returned to the cell-containing fermentor.

The augmentation loop aspect of the present invention is adaptable also to optimizing parameters of cell growth or output such as to increase the production of a particular protein. Experiments have demonstrated that the augmentation loop aspect of the invention can be utilized with cultures of other cells that are transformed or that do not comprise a range or plurality of cell types. For example, the growth and output of cultures of VERO (African Green Monkey Kidney) cells as described under ATCC Catalog No. ATCC CCL 81, CHO (Chinese Hamster Ovary) and other carrier-bound cells, and CV-1 cells can be increased by use of the augmentation loop aspect of the present invention.

The present method provides also for the use of one or more substances to inactivate the added protease to eliminate or attenuate any negative effects which the protease may have on the cultured cells. For instance, after incubation of the cells with trypsin, trypsin inhibitor can be added to the culture media in order to inactivate the trypsin to thereby eliminate the negative or toxic effects of the trypsin. The inactivator can also be provided in an immobilized form, e.g., in a column or on another type of inert substrate.

The present invention also relates to the advantageous aspect of altering the susceptibility of a virus strain to a protease such as trypsin in the event that a strain should arise which cannot be activated by standard methodologies. There are several structural properties of the HA that determine the differential cleavability, but the key factor is the amino acid sequence at the cleavage site. It has been demonstrated that susceptibility of hemagglutinin to cleavage is not a fixed characteristic of the molecule. The present invention provides advantageously for the alteration of hemagglutinin to ensure its susceptibility to cleavage by available proteases.

Specifically, hemagglutinin can be altered by adaptation of a subject virus to a novel host cell. Cleavability of the hemagglutinin of the adapted virus in a new host cell type can sometimes be obtained by a single amino acid substitution close to the cleavage site. Thus, alterations in the cleavability of the HA of a particular virus strain may be generated by known site-directed mutagenesis techniques. By employing these techniques in the present invention, virtually any influenza virus strain could be modified to be susceptible to enzyme activation. Thus, the methodology of the present invention allows the large scale production of many viruses to a high titre.

In one embodiment, the present invention utilizes CEC aggregates which have been modified but still share some of the characteristics of cell culture systems used to propagate viruses such as the TBE virus. Specifically, the present method employs a cell culture system which comprises modified CEC cell aggregates having a diameter between 100 μm and 1000 μm, wherein the aggregates are derived from an entire vertebrate embryo, such as a chicken, without removal of the brain and inner organs. Because of this, a plurality of cell types are available, that is, cells which are derived from several, many or all of the embryonic tissues and organs of the vertebrate embryo.

The significance of this aspect of the invention is illustrated by the fact that different virus strains are able to replicate to different extents depending on the cell type in which the virus is cultured. For example, the three cell layers of the avian chorioallantoic membrane originate from three different embryonic origins. The chorionic epithelium differentiates from the ectoderm, the mesenchymal cells of the connective tissue from the mesoderm and the allantoic epithelium from the ectoderm.

In accordance with the invention, cultures can be established with a CEC biomass of about 30 g/L. The cultures are then infected with virus grown conventionally in embryonated eggs or other suitable sources. Screening experiments are carried out in spinner cultures, which are cultures in which rotating mechanical agitation is provided to the media so that cells growing therein remain suspended and exposed continuously to well-mixed media. Spinner cultures with a volume of 100 ml can be used without appreciable loss of titre. As seen in Table 1, a number of strains (for example, B. Mass., B. Panama, Brazil, USSR) have been successfully cultured using this system, with hemagglutination (HA) titres being obtained close to the level obtained in the allantoic fluid of the embryonated egg.

A major advantage of the present CEC culture methodology of the present invention is that virus production occurs over a period of 3–4 days so that half of the medium volume can be harvested each day before harvesting the total volume on the final day, that is, a total volume of up to 5 liters can be generated from a 2 liter culture vessel. However, a number of strains could not be successfully activated using this system. Attempts were made to activate these strains by the addition of various proteases.

Two proteases are known that are involved in the cleavage of influenza HA-protein, trypsin, Klenk and Rott, *The Molecular Biology of Influenza Virus Pathogenicity*, Academic Press (1975) and Subtilisin A, Barr, Cell, 66 1–3, (1991); Stieneke-Gröber et al., *Influenza Virus Hemagglutinin with Multibasic Cleavage Site is Activated by Furin, a Subtilisin-Like Endoprotease*, EMBO 11, 2407–2414 (1992). Table 1 summarizes the results obtained by the addition of trypsin and Subtilisin A to a CEC culture medium. Strains such as B/Yamagata, Taiwan, Singapore and all H3N2 strains tested could be successfully activated by the addition of trypsin or Subtilisin A to generate titres close to those obtained by cultivation in the embryonated egg. One strain, California, is only activated by Subtilisin A, but not by trypsin. Some strains e.g., Brazil, are inhibited by the addition of trypsin.

In the augmentation loop aspect of the method of the present invention, high concentrations of trypsin or other exogenous enzymes can indeed be utilized to augment virus activation. Specifically, following incubation of media containing infected cells and virus in the loop, the trypsin or other enzymes are neutralized at intervals by trypsin inhibitors or by inhibitors for the enzyme used. This aspect of the invention allows a higher degree of activation compared to other methods which employ lower concentrations of trypsin and, because the trypsin is neutralized at regular intervals, allows continuous production and harvesting of the virus rather than batch production and a single harvest. Brown also does not recognize the advantages of the use of enzymes of the subtilisin family which can be used at high concentrations without detrimental effect on the cells, nor does Brown comprehend the use of a virus modified to make it more susceptible to proteases.

The present invention provides also for the continuous or periodic monitoring of the growth, infection and activation levels of the cells in the culture. The monitoring can be by automated or other means and results of the monitoring can be used to vary the conditions of the culture or augmentation loop in order to maximize desired parameters such as growth, infection and activation levels.

From the foregoing, it can be seen that advantages of the present method over methods employing whole embryos and over previous culture methods in the field are several. One advantage is that the presently claimed method allows commercial production of influenza virus substantially free of egg proteins. Another advantage is that the present invention is adapted to include the small-size aggregate aspect of cultures which were specifically developed for culturing the Tick Borne Encephalitis Virus ("TBEV").

Moreover, the method of the present invention is capable of automation, requires relatively little labor when compared with conventional culture techniques employing chicken embryos, and is much less susceptible to contamination because of its fewer process steps. In addition, the present method produces a much higher virus titre when compared with other cell culture methods.

The present invention provides a method which enables the growth of all human influenza virus strains tested to levels approaching that obtained in the embryonated egg. As Table 1 shows, all human influenza virus strains tested were grown to titres approximating those obtained in the embryonated egg. No virus grown in eggs produced more than eight times the amount of HA antigen than viruses grown in biomass culture according to the present method.

Another advantage of the present invention over the embryonated egg can be seen when the total antigen yield per egg for each system is compared. For example, one embryonated egg yields 5–7 ml allantoic fluid which is harvested 48–72 hours after inoculation. Four embryonated eggs are required to generate 200 ml of biomass culture. The biomass culture can be continuously harvested to generate 400–500 ml of virus-containing medium over a period of 96 hours. Therefore the biomass culture provides 100 ml antigen per egg compared to a maximum of 7 ml from the inoculated egg, i.e., a 14-fold increase. It can thus be seen with clarity that the present method produces a higher antigen yield when compared with the embryonated egg method. This advantage of the present invention is illustrated further by the data presented in Table 2.

The method of the invention provides additional advantages over the use of embryonated eggs. In particular, the invention can be upscaled to allow use of fermentors with volumes on the order of 100–1000 liters. Moreover, the method can be automated, requires little labor and is much less susceptible to contamination because of its process steps when compared to those required utilizing embryonated eggs. Table 3 demonstrates the effective scale up of the invention from 100 ml cultures to an automated 2 liter fermentor. The fermentor culture using trypsin activation includes an augmentation loop feature whereby virus-containing media is continuously removed from the fermentor to a vessel containing trypsin where virus is activated over a period of approximately one hour. The trypsinized culture is then pumped into a vessel containing trypsin inhibitor and the virus-containing media with the neutralized trypsin is then returned to the fermentor for a further cycle of replication. High concentrations of trypsin or other proteases in conventional methods would have detrimental effects on the cell culture and virus, if incubated with them over a prolonged period. The augmentation loop aspect of the invention allows activation of the virus with much higher concentrations of trypsin than can be used in other culture methods. Table 3 shows the advantage of this method for the virus strain California which can only be activated by trypsin using the augmentation loop with trypsin inhibitor.

Moreover, the present method produces approximately equal or higher yields than conventional cell culture methods. Table 4 demonstrates the yield of HA antigen obtained for different strains of influenza A and a B strain in MDCK cell culture, standard CEC culture and CEC biomass aggregates in the presence and absence of trypsin and subtilisin. B/Panama and Brazil are examples of viruses that can be grown to higher titre in biomass culture without trypsin or subtilisin than in standard CEC culture with or without trypsin. Slightly higher titres can be obtained in MDCK cultures i.e., in a cell line not suitable for human vaccine production. Activation of California, Singapore 6, Hong Kong, Hong Kong 5 and Beijing by trypsin or subtilisin leads to titres higher than those obtained with or without activation in standard CEC cultures or in MDCK culture. The advantages of the present invention are aptly illustrated in the following examples. These examples do not limit the scope of invention.

EXAMPLE 1

Hemagglutinin titre obtained from various influenza strains produced by embryonated eggs and-spinner culture with or without proteases Influenza strains listed in Table 1 were used either for infection of embryonated chicken eggs or the CEC spinner culture.

The CEC-spinner culture aggregates were produced as disclosed in U.S. Pat. No. 5,391,491, PCT application WO 91/09937, the disclosure of which is incorporated herein by reference in its entirety. In one embodiment, the present invention utilizes a plurality of cell types obtained from a plurality of avian embryo tissues. Two embryonated eggs are required to generate 100 ml of biomass culture. 100 ml CEC spinner culture were infected with 1 ml of influenza virus containing allantoic fluid. Addition of the protease was immediately carried out after infection. Either Trypsin (Seromed) or Subtilisin A (Fa. Novo) were added to the medium to a concentration of 20 mU/ml and 30 ug/ml, respectively. The CEC spinner culture was incubated for 3–4 days with removal of the half of the medium volume (50 ml) every day. Fresh medium with or without protease was added to an end volume of 100 ml culture. After 4 days of incubation and daily harvesting of virus containing medium the pooled cell culture medium was collected and the HA-titre was determined. The HA-titre was determined as described by Hirst (1941) and Barrett et al. (1993).

10–11 days old embryonated eggs were infected with 200 µl virus containing allantoic fluid per egg. Infected eggs were incubated for 2–3 days at 37° C. as described by Burnett et al. (1940). The egg was opened and the HA titre was determined as already described.

Table 1 compares the hemagglutinin titre obtained from various influenza strains produced by embryonated eggs and spinner culture with or without proteases. Thus, it can be seen that the use of the CEC spinner culture and the addition of protease according to the present invention increases the yield of the most strains to that approaching the yields of virus strains grown in the embryonated egg cultures without the disadvantages inherent in other culture methods.

TABLE 1

Maximum HA-Titre obtained for different Influenza strains in embryonated eggs and in CEC-spinner-cultures with and without the proteases Trypsin and Subtilisin A

| | | | HA-Titre | | | |
|---|---|---|---|---|---|---|
| | | Vaccine | CEC spinner culture/Protease | | | |
| Subtype | Strain | Year | none | Trypsin | Subtilisin A | Egg |
| B | B/Massachusetts | | 7 | 8 | n.d. | 9 |
| | B/Panama | 1991/92, 92/93 | 6 | 4 | 5 | 8 |
| | B/Yamagata | 1990/91, 91/92, 92/93 | 3 | 5 | 5 | 8 |
| A/H1N1 | Brazil | | 7 | 1 | n.d. | 10 |

TABLE 1-continued Maximum HA-Titre obtained for different Influenza strains in embryonated eggs
and in CEC-spinner-cultures with and without the proteases Trypsin and Subtilisin A

|  |  |  | HA-Titre | | | |
|---|---|---|---|---|---|---|
|  |  | Vaccine | CEC spinner culture/Protease | | | |
| Subtype | Strain | Year | none | Trypsin | Subtilisin A | Egg |
|  | California |  | 2 | 2 | 6 | 8 |
|  | USSR |  | 7 | 2 | n.d. | 10 |
|  | Singapore 6 | 1990/91, 91/92, 92/93 | 2 | 4 | 4 | 7 |
|  | Taiwan | 1991/92 | 4 | 6 | 4 | 9 |
|  | Texas 36 | 1992/93 | 5 | 4 | n.d. | 6 |
| A/H2N2 | A2 Singapore |  | 2 | 7 | n.d. | 9 |
| A/H3N2 | Hong Kong |  | 2 | 8 | 6 | 10 |
|  | Hong Kong 5 |  | 2 | 7 | 6 | 8 |
|  | Texas |  | 2 | 6 | n.d. | 8 |
|  | Victoria |  | 2 | 6 | n.d. | 8 |
|  | Guizho | 1990/91 | 2 | 6 | 5 | 6 |
|  | Shanghai 16 | 1990/91 | 2 | 6 | 6 | 6 |
|  | Beijing | 1991/92, 92/93 | 2 | 6 | 6 | 8 | n.d. = not done Dr. O. Kistner

EXAMPLE 2

Virus yield obtained from various influenza strains produced by embryonated eggs and CEC biomass culture Embryonated eggs and biomass CEC spinner culture were infected with various strains of influenza virus as listed in Table 2 and described in example 1.

The embryonated egg yields a maximum of 7 ml allantoic fluid which is harvested 72 h post inoculation. Two embryonated eggs are required to produce 100 ml of biomass culture. By harvesting half of the culture volume after 48 and 72 h and the total volume after 96 h, 200 ml of virus containing medium was collected over a 96 h period. Therefore the biomass culture provides 100 ml virus antigen per egg compared to a maximum of 7 ml from the inoculated egg e.g., 14 fold volume more. When this factor is taken into account the present method produces a higher virus antigen yield when compared with the embryonated egg method. This is illustrated by the calculations in Table 2.

Table 2 compares the virus yield obtained from various influenza strains produced by embryonated eggs and by those produced by the present invention. The HA-titre was calculated as already described for 100 ml of biomass spinner culture medium obtained from one egg and 7 ml of allantoic fluid per egg. Thus, the data in Table 2 present the total virus yield per egg in CEC spinner culture obtained with or without proteases, calculated from the results of Example 1. Dependent on the influenza strain used the biomass spinner culture method results in an approx. 2–14 fold increase in virus antigen compared to the yield obtained in the embryonated egg. Incubation of the infected biomass spinner culture without the addition of a protease reached a virus yield close to that obtained in eggs for B-Panama, Brazil, USSR and Texas 36 which could not be increased by the protease. The virus yield of all other influenza virus strains was increased by the addition of a protease in comparison to the biomass without exogenous addition of a protease. Thus, insufficient endogenous protease content of the biomass cell culture can be overcome by the exogenous addition of a protease to activate the viral hemagglutinin.

TABLE 2

Comparison of Virus Yield in Embryonated Egg and Biomass Culture
Total Yield/Egg

|  |  | Biomass Culture | | Egg | Ratio |
|---|---|---|---|---|---|
| Subtype | Strain | Protease | HA Units × 100 ml | HA Units × 7 ml | Biomass Culture/Egg |
| B | B/Mass. | T | 25600 | 3584 | 7.1 |
|  | B/Panama | N | 6400 | 1792 | 3.6 |
|  | B/Yamagata | T | 3200 | 1792 | 1.8 |
| A/H1N1 | Brazil | N | 12800 | 7168 | 1.8 |
|  | California | S | 6400 | 1792 | 3.6 |
|  | USSR | N | 12800 | 7168 | 1.8 |
|  | Singapore 6 | T | 1600 | 896 | 1.8 |
|  | Taiwan | T | 6400 | 3584 | 1.8 |
|  | Texas 36 | N | 3200 | 448 | 7.1 |
| A/H2N2 | A2 Singapore | T | 12800 | 3584 | 3.6 |
| A/H3N2 | Hong Kong | T | 25600 | 7168 | 3.6 |

TABLE 2-continued

Comparison of Virus Yield in Embryonated Egg and Biomass Culture
Total Yield/Egg

| Subtype | Strain | Biomass Culture | | Egg | Ratio |
| | | Protease | HA Units × 100 ml | HA Units × 7 ml | Biomass Culture/Egg |
| --- | --- | --- | --- | --- | --- |
| | Hong Kong 5 | T | 12800 | 1792 | 7.1 |
| | Texas | T | 6400 | 1792 | 3.6 |
| | Victoria | T | 6400 | 1792 | 3.6 |
| | Guizho | T | 6400 | 448 | 14.3 |
| | Shanghai 16 | T | 6400 | 448 | 14.3 |
| | Beijing | T | 6400 | 1792 | 3.6 |

N: none
T: Trypsin
S: Subtilisin A

EXAMPLE 3

Large scale-up of influenza virus production in CEC fermentor cultures

A scale-up of the 100 ml spinner culture to an automated 2 liter fermentor was performed. A 2 liter fermentor of biomass cell culture was inoculated with 2 ml influenza virus containing allantoic fluid with an HA titre of 6–8 with continuous medium changes at 37° C.

The method of the invention using large scale fermentor culture employs trypsin activation in an augmentation loop system whereby portions of the media containing the desired virus are continuously removed from the fermentor to a vessel containing trypsin or any other required protease. In the vessel containing trypsin or subtilisin A with a concentration of 20 mU/ml and 30 μg/ml respectively the virus is activated over a period of approximately one hour. The medium containing the trypsin activated virus is then pumped into a vessel containing soja bean trypsin inhibitor (Sigma) for about 1 h with a concentration of sufficient to neutralize the residual trypsin activity. The medium containing neutralized trypsin with virus is then returned to the fermentor for a further cycle of replication. By continuous removal of the biomass cell culture medium from the fermentor and addition of fresh culture medium 4–5 l of virus containing medium was obtained during a time period of 96 h. The method of the invention allows activation of virus with much higher concentration of trypsin than would be possible with conventional methods where high concentrations of the protease would have detrimental effects on the cell culture and virus, if incubated with them over a prolonged period.

Table 3 shows the advantages of the method for the virus strain California which can only be activated by trypsin using the augmenter loop system and trypsin inhibitor.

TABLE 3

Maximum HA-Titre obtained for different Influenza strains in 100 ml CEC-spinner cultures and 2 liter CEC-fermentor cultures

| | | Vaccine | HA - Titre | | | |
|---|---|---|---|---|---|---|
| | | | CEC culture | | | |
| Subtype | Strain | Year | Protease | spinner | fermentor | Egg |
| B | B/Panama | 91/92, 92/93 | N | 6 | 6 | 8 |
| A/H1N1 | Brazil | | N | 7 | 7 | 10 |
| | California | | S | 6 | 6 | 8 |
| | | | T | 2 | 6 | |
| | Singapore 6 | 90/91, 91/92, 92/93 | S | 4 | 4 | 7 |
| | | | T | 4 | 4 | |
| A/H3N2 | Hong Kong 5 | | S | 6 | 6 | 8 |
| | | | T | 7 | 7 | |
| | Beijing | 91/92, 92/93 | S | 6 | 7 | 8 |
| | | | T | 6 | 7 | |

N: none
S: Subtilisin A
T: Trypsin

EXAMPLE 4

Comparison of HA titre of Influenza virus in MDCK cell culture, standard CEC culture and CEC biomass aggregates Embryonated eggs, CEC fermentor culture, CEC and MDCK monolayer cultures were infected with influenza virus strains as listed in Table 4. Infection of embryonated eggs were performed as described in Example 1 and of fermentor culture as described in Example 3. Primary chicken embryo cells were propagated as described by Mayr and Kalcher (1961) and infected with influenza virus containing allantoic fluid with a HA titre of 6–8.

Continuous cell lines of MDCK cells were propagated as monolayers and infected with influenza virus containing allantoic fluid with a HA titre of 6–8. Incubation was carried out until development of maximum cytopathic effect (CPE) or for a maximum of 72 h, and HA-titre was determined as previously described.

These data demonstrate that the method of invention produces higher yields for all viruses studied in the CEC fermentor culture than in CEC monolayer culture than other cell culture methods. Table 4 compares the HA titre obtained for different strains of influenza A and a B strain in MDCK cell culture, standard CEC culture and CEC biomass aggregates in the presence and absence of trypsin and subtilisin A. Slightly higher titres can be obtained in MDCK cultures, i.e., in cells not licensed for human vaccine production. Activation of California, Singapore 6, Hong Kong, Hong Kong 5 and Beijing by trypsin or subtilisin leads to titres higher than those obtained with or without activation in standard CEC cultures or in MDCK culture.

These data demonstrate that there is no significant difference in the HA1 and ELISA antibody titres generated by immunization with four different influenza strains grown by standard egg technology and those produced according to the claimed invention.

TABLE 4

Comparison of HA titres of Various Influenza Strains in CEC Biomass Cultures, CEC Monolayer Cultures and MDCK Monolayer Cultures with and without addition of Proteases with titres in embryonated eggs

| | | | HA-Titre | | | | | | | |
|---|---|---|---|---|---|---|---|---|---|---|
| | | | | | | Tissue culture "monolayer"/Protease | | | | |
| | | Vaccine | CEC fermentor - culture | | | CEC | | MDCK | | |
| Subtype | Strain | Year | None | Trypsin | Subtilisin A | None | Trypsin | None | Trypsin | Egg |
| B | B/Panama | 91/91; 92/93 | 6 | 4 | 5 | 2 | 2 | 7 | 7 | 8 |
| A/H1N1 | Brazil | | 7 | 1 | n.d. | 5 | 5 | 8 | 8 | 10 |
| | California | | 2 | 6 | 6 | 2 | 2 | 5 | 5 | 8 |
| | Singapore 6 | 90/91; 91/92; 92/93 | 2 | 4 | 4 | 0 | 0 | 3 | 2 | 7 |
| A/H3N2 | Hong Kong | | 2 | 8 | 6 | 2 | 5 | 6 | 6 | 10 |
| | Hong Kong 5 | | 2 | 7 | 6 | 0 | 0 | 4 | 5 | 8 |
| | Beijing | 91/92; 92/93 | 2 | 7 | 7 | 2 | 2 | 5 | 6 | 8 | n.d. = not done

EXAMPLE 5

Comparison of Antibody Response after Immunization with Influenza Virus Vaccines Derived From Conventional Methods with the Response Produced by Vaccines According to the Invention The influenza A strains Brazil (H1N1), California (H1N1) and Hong Kong (H3N2) and the B strain B/Panama were grown in embryonated eggs as previously described and the allantoic fluids were harvested, pooled and frozen at −80° C. The same strains were grown also in a CEC biomass fermentor culture according to the claimed invention. The tissue culture medium supernatant was concentrated by ultrafiltration using a 100,000 M.W. cut-off filter and this material and the allantoic fluid from embryonated cells were purified by ultracentrifugation over a 20% sucrose cushion. The virus pellets were resuspended in buffer and inactivated by U.V./psoralene treatment (10 µg/ml 4-aminoethyltrioxalen Hydrochloride, U.V. intensity of 20 mW/cm$^2$) for 15 minutes. The antigen preparations were then diluted to give a concentration of 20 µg/ml and adjuvanted with Al(OH)$_3$.

Groups of ten mice were then immunized with a dose of 10 µg antigen from embryonated eggs and boostered with the same dose four weeks later. Two weeks after the booster injection, the animals were sacrificed and serum HA1 titre and ELISA titre of the group was determined. The identical procedure was performed also with 10 µg of antigen produced according to the claimed invention. Results are shown in Table 5.

TABLE 5

Comparison of Antibody Response in Mice (Pool of 10 immunized mice each) After Immunization with Vaccines Produced in Embryonated Eggs and Mice Immunized with Vaccines Produced in a CEC Biomass Fermentor

| | | Embryonated Egg | | | Fermentor | |
|---|---|---|---|---|---|---|
| | | Antibody Titre | | | Antibody Titre | |
| Subtype | Strain | HAI | ELISA | Protease | HAI | ELISA |
| A/H1N1 | Brazil | 2560 | 102400 | — | 2560 | 102400 |
| | California | 2560 | 51200 | S | 5120 | 102400 |
| A/H3N2 | Hong Kong 5 | 2560 | 204800 | T | 2560 | 102400 |
| B | B/Panama | 160 | 102400 | — | 160 | 102400 |

—: none
T: Trypsin
S: Subtilisin A

Through use of the augmentation loop aspect of the invention, the set of conditions for optimal growth of cells in a culture system are provided separately from the set of conditions required for the efficient stimulation or activation of specific cellular processes. The augmentation loop aspect of the invention is thereby advantageous in several respects. In one respect, the loop provides an advantage in that it separates the two sets of conditions when they would counteract or work against one another. For example, when one set of conditions for the stimulation of a particular cellular function would have a negative or toxic effect on the growth of the cells, i.e., treatment of cells with high concentrations of trypsin, the augmentation loop provides a means for separating the treatment conditions from the culturing conditions in the fermentor.

Thus, cells can be cultured in a growth vessel having optimal growth conditions. During growth, the media, cells or both can be removed into the augmentation loop for treatment under different conditions to induce or activate desired cellular activities such as the production of a virus or a recombinant protein. The loop can comprise either one or more additional vessels or columns or combinations thereof. For instance, the conditions for induction such as the addition of an inductor, an increase in temperature over that of the growth vessel, a change of pH or osmolarity, or the removal of the desired product to prevent feedback inhibition can be provided in a second vessel comprising the augmentation loop. After activation, the transferred media, cells or both can be further transferred to a third vessel or column of the loop system for further augmentation of the cells by, e.g., inactivation of the activator by an inhibitor, or a pH change. The medium, cells or both can then be returned to the growth vessel. In sum, the present invention provides a method for producing efficiently viruses and vaccines therefrom utilizing vertebrate cell aggregates.

The description, figures and examples provided herein, while indicating preferred embodiments of the invention, are given by way of illustration and are not intended to limit the present invention. Various changes and modifications within the spirit and scope of the invention will become apparent to those skilled in the art upon reading the instant specification.

What is claimed is:

1. A method for producing Influenza virus, comprising the steps of:
   (a) infecting with Influenza virus a culture of cell aggregates comprising avian embryo cells;
   (b) incubating the culture of cell aggregates infected with Influenza virus to propagate the virus to form a virus-containing medium;
   (c) removing a first portion of said virus-containing medium;
   (d) adding to the removed first portion of step (c) at least one serine protease, and then incubating the portion for a length of time sufficient to achieve activation of the Influenza virus;
   (e) removing a second portion of the first portion of step (d) and adding to the second portion at least one compound that inhibits or attenuates any cell toxic effects of the serine protease of step (d) and incubating said second portion for a length of time sufficient to achieve a desired level of inhibition or attenuation;
   (f) removing a third portion of the second portion of step (e) and returning it to the culture of cell aggregates of step (a).

2. The method according to claim 1, wherein step (a) occurs in a first vessel and step (d) occurs in a second vessel and step (e) occurs in a third vessel.

3. The method according to claim 2, wherein said first vessel is connected to said second vessel and said second vessel is connected to said third vessel and said third vessel is connected to said first vessel such that the producing can be performed as a continuous loop.

4. The method according to claim 1, wherein the avian embryo cells are chicken cells.

5. The method according to claim 1, wherein the cell aggregates have a diameter between about 100 mm and 1000 mm.

6. The method according to claim 1, wherein the serine-protease is selected from the group consisting of trypsin, chymotrypsin, thermolysin, pronase and subtilisin A.

7. The method according to claim 1, wherein the serine protease is immobilized on a carrier.

8. The method according to claim 1, wherein the compound that inhibits or attenuates any cell toxic effects of the serine protease is a protease inhibitor.

9. The method according to claim 8, wherein the protease inhibitor is selected from the group consisting of soybean trypsin inhibitor, egg trypsin inhibitor and aprotinin.

10. The method according to claim 1, wherein the compound that inhibits or attenuates any cell toxic effects of the serine protease is immobilized on a carrier.

11. The method according to claim 1, wherein the system is an augmentation loop system.

12. The method according to claim 11, further comprising the steps of:
   (g) monitoring (i) the growth levels of Influenza virus in the cell aggregates, (ii) the activation levels of Influenza virus by the substance that cleaves Influenza hemagglutinin, and (iii) the inhibition levels of said Influenza virus; and
   (h) varying the conditions of the culture to maximize the growth, activation and inhibition levels.

13. A method of producing an Influenza vaccine comprising the steps of:
   (a) infecting with Influenza virus a culture of cell aggregates comprising avian embryo cells;
   (b) incubating the culture of cell aggregates infected with Influenza virus to propagate the virus to form a virus-containing medium;
   (c) removing a first portion of said virus-containing medium;
   (d) adding to the removed first portion of step (c) at least one serine protease, and then incubating the first portion for a length of time sufficient to achieve activation of the Influenza virus;
   (e) removing a second portion of the first portion of step (d) and adding to the second portion at least one compound that inhibits or attenuates any cell toxic effects of the serine protease of step (d) and incubating said second portion for a length of time sufficient to achieve a desired level of inhibition or attenuation;
   (f) removing a third portion of the second portion of step (e) and returning it to the culture of cell aggregates of step (a);
   (g) harvesting virus from the culture of cells of step (f); and
   (h) preparing a vaccine with said harvested Influenza virus of step (g).

* * * * *